(12) United States Patent
Shioya et al.

(10) Patent No.: US 7,691,828 B2
(45) Date of Patent: Apr. 6, 2010

(54) COMPOSITIONS FOR AMELIORATING FECAL PROPERTIES

(75) Inventors: Yasushi Shioya, Tokyo (JP); Wataru Okawa, Tokyo (JP); Yasushi Kajihara, Tokyo (JP)

(73) Assignee: Kao Corporation, Tokyo (JP)

( * ) Notice: Subject to any disclaimer, the term of this patent is extended or adjusted under 35 U.S.C. 154(b) by 1146 days.

(21) Appl. No.: 10/505,883

(22) PCT Filed: Mar. 5, 2002

(86) PCT No.: PCT/JP02/02022

§ 371 (c)(1),
(2), (4) Date: Jan. 10, 2005

(87) PCT Pub. No.: WO03/074040

PCT Pub. Date: Sep. 12, 2003

(65) Prior Publication Data

US 2005/0113333 A1     May 26, 2005

(51) Int. Cl.
*A61K 31/715* (2006.01)
*A61K 31/19* (2006.01)

(52) U.S. Cl. .......................... 514/54; 514/57; 514/568; 514/569

(58) Field of Classification Search .................... 514/54, 514/568, 569, 57
See application file for complete search history.

(56) References Cited

U.S. PATENT DOCUMENTS 5,770,217 A * 6/1998 Kutilek et al. ............... 424/442

6,632,459 B2 * 10/2003 Graus et al. .................. 424/728
2002/0054924 A1 * 5/2002 Leahy et al. ................. 424/732

FOREIGN PATENT DOCUMENTS

| JP | 2-249952 | 10/1990 |
|---|---|---|
| JP | 2000-232855 | 8/2000 |
| JP | 2001-120227 | 5/2001 |
| JP | 2002-53464 | 2/2002 |
| WO | WO 91/08680 | 6/1991 |
| WO | WO 01/78522 A2 | 10/2001 |
| WO | WO 01/82724 A2 | 11/2001 |

\* cited by examiner

*Primary Examiner*—Shaojia Anna Jiang
*Assistant Examiner*—Everett White
(74) *Attorney, Agent, or Firm*—Oblon, Spivak, McClelland, Maier & Neustadt, L.L.P.

(57) ABSTRACT

Provided is a fecal condition improving composition containing (a) a compound selected from the group consisting of caffeic acid, chlorogenic acid and ferulic acid, esters thereof, and pharmaceutically acceptable salts thereof, (b) a water-soluble and hardlyfermentable dietary fiber, and (c) a water-soluble and fermentable dietary fiber.

The composition of the present invention is useful as a food or beverage, or a pharmaceutical for improving the fecal condition of humans or animals, more specifically, inhibiting intestinal clamping due to imbalance of the autonomic nervous system caused by psychological stress or dietary change, suppressing abdominal pain or discomfort, improving the fecal condition, and ameliorating constipation.

7 Claims, No Drawings

COMPOSITIONS FOR AMELIORATING FECAL PROPERTIES

TECHNICAL FIELD

The present invention relates to a fecal condition improving composition having high safety and excellent fecal condition improving action and being useful for the treatment of irritable bowel syndrome.

BACKGROUND ART

Of abdominal disorders, irritable bowel syndrome (IBS) is a functional disorder having, as symptoms, abnormal bowel movement (diarrhea, constipation) and digestive symptoms (abdominal pain, abdominal bloating). In Japan, the number of patients suffering from it including latent patients is said to be about 20% of the entire population over 15 years old. Causes of IBS have not been elucidated yet, but psychological stress and dietary habit are considered to be closely involved in it. The number of patients suffering from this disease will continue to grow in view of the modern society featured by rapid dietary change and abundant psychological stress. In addition, abnormal defecation due to psychological stress is said to be observed more frequently even in animals such as pets in recent days.

There is accordingly a demand for the development of a fecal condition improver which has high safety, can be administered daily without imposing a strain on patients, and ameliorates constipation or diarrhea of humans or animals due to psychological stress.

DISCLOSURE OF THE INVENTION

The present inventors have carried out various investigations with a view to discovering a component having a fecal condition improving action among components which we can take daily. As a result, it has been found that a composition having a marked effect for ameliorating diarrhea and constipation can be obtained by using a plant-derived component such as caffeic acid or chlorogenic acid and two dietary fibers in combination.

In one aspect of the present invention, there is thus provided a fecal condition improving composition, which contains the following components (a), (b) and (c):

(a) a compound selected from the group consisting of caffeic acid, chlorogenic acid and ferulic acid, esters thereof, and pharmaceutically acceptable salts thereof, (b) a water-soluble and hardly-fermentable dietary fiber, and (c) a water-soluble and fermentable dietary fiber.

In another aspect of the present invention, there is also provided use of the components (a), (b) and (c) for the preparation of a fecal condition improving composition.

In a further aspect of the present invention, there is also provided a fecal condition improving method, which contains administering an effective amount of a composition comprising the above-described components (a), (b) and (c).

BEST MODE FOR CARRYING OUT THE INVENTION

As Component (a) to be used in the present invention, natural products containing it, preferably plant extracts can be used. Examples of the plant include coffee, onion, radish, lemon, Jew's marrow, *Cnidium Rhizome*, Japanese angelica root, pine, *Coptis Rhizome, Asafoetida, Nader Spikenar*, corn, barley, and rice.

The caffeic acid and chlorogenic acid may be extracted from plants such as coffee beans, nandina leaves, unripe apples, sunflower seeds, burdocks, eggplant skins, and plums. For example, a component extracted from seeds of *Coffea Arabica* LINNE with an aqueous solution of an acid such as ascorbic acid or citric acid upon warming or hot water is preferred, of which extracts from raw coffee beans, unripe apples or plums are more preferred.

Ferulate esters are compounds contained in natural products such as rice and adlai, especially plant. It is available as a purified product of a plant or an industrially synthesized product. A ferulate ester can be obtained, for example, in the following manner. A rice bran oil obtained from rice bran is separated by hydrous ethanol and hexane in a weak alkaline environment at room temperature and then, a ferulate ester is obtained from the hydrous ethanol fraction. Ferulic acid can be obtained by hydrolyzing the ferulate ester obtained in the above-described step with sulfuric acid under pressure and heating, followed by purification. It is also available by culturing bacteria (*Pseudomonas*) in a culture medium containing a clove oil, which has been obtained by steam distillation of buds and leaves of *Syzygium aromaticum* MERRILL et PERRY or in an eugenol-containing culture medium obtained by purifying a clove oil and then, separating and purifying the resulting culture medium. When ferulic acid is prepared by chemical synthesis, condensation reaction between vanillin and malonic acid can be employed for it (Journal of American Chemical Society, 74, 5346, 1952).

Caffeic acid, chlorogenic acid or ferulic acid, or pharmaceutically acceptable salt thereof has its steric isomers. In the present invention, pure steric isomers or mixtures thereof can be used.

The esters of caffeic acid, chlorogenic acid or ferulic acid embrace natural esters, preferably those contained essentially in plants, those converted through chemical treatment upon extraction and/or fractionation, and chemically modified ones. Examples include esters between a $C_{1-40}$ alcohol and the above-described acid, more specifically esters between a linear or branched alkyl or alkenyl alcohol, allyl alcohol, terpene alcohol, sterol or trimethylsterol and the above-described acid.

Caffeic acid, chlorogenic acid or ferulic acid used in the form of its pharmaceutically acceptable salt has improved water solubility and enhanced physiological effectiveness. Examples of the base substance to be used for the formation of such pharmaceutically acceptable salt include inorganic bases, for example, hydroxides of an alkali metal or alkaline earth metal such as lithium hydroxide, sodium hydroxide, potassium hydroxide, magnesium hydroxide and calcium hydroxide, and ammonium hydroxide; basic amino acids such as arginine, lysine, histidine and ornithine; and organic bases such as monoethanolamine, diethanolamine and triethanolamine. Among them, preferred ones are hydroxides of an alkali metal or alkaline earth metal. After preparation of these salts, they may be added to the invention product. Alternatively, salt forming components can be added to the invention product separately and then reacted in a formulation system.

Two or more compounds may be used in combination as Component (a) of the present invention. As Component (a), natural extracts are preferred.

Examples of the water-soluble and hardly-fermentable dietary fiber (Component (b)) to be used in the present invention include sodium alginate, molecular-weight-reduced alginate salts (such as sodium salt and potassium salt), molecular-weight-reduced alginate esters, carrageenan, fucoidan, laminaran, carboxymethylcellulose sodium, polydextrose and agar. Of these, molecular-weight-reduced alginic acid, molecular-weight-reduced alginate salts and polydextrose are preferred because its aqueous solution has a low viscosity.

Examples of the water-soluble and fermentable dietary fiber (Component (c)) include pectin, molecular-weight-reduced pectin, guar gum, molecular-weight-reduced guar gum, molecular-weight-reduced hemicellulose, gum arabic, konjak mannan, locust bean gum, pullulan, curdlan, xanthan gum, gellan gum and indigestible dextrin. Of these, molecular-weight-reduced pectin, molecular-weight-reduced guar gum, molecular-weight-reduced hemicellulose, gum arabic, pullulan and indigestible dextran are preferred because its aqueous solution has low viscosity. Of these, molecular-weight-reduced hemicellulose, molecular-weight-reduced guar gum and indigestible dextrin are more preferred. As the molecular-weight-reduced hemicellulose, that derived from wheat, soybean, corn or the like can be used. That derived from corn is desired because its abnormal taste or abnormal odor due to raw materials is not severe, it does not contain much foreign substances such as saponin and it involves less problems upon production such as foaming upon preparation. Molecular-weight-reduced hemicellulose adjusted to have a weight-average molecular weight of 200000 or less is more preferred because its aqueous solution has low viscosity. The weight-average molecular weight of hemicellulose can be reduced to 200000 or less in a conventional manner, for example, by acting an enzyme on high molecular hemicellulose or through thermal decomposition or pressurized decomposition.

The present invention is characterized in that three components (a), (b) and (c) are used in combination. A composition having any one or two of these three components cannot attain sufficient fecal condition improving effect. A weight ratio of Component (a) to the total amount of Components (b) and (c), that is, $(a)/[(b)+(c)]$ preferably falls within a range of from 1/1000 to 10/1, more preferably from 1/200 to 1/2 from the viewpoint of fecal condition improving effect. Component (a) is added to the invention composition preferably in an amount of from 0.001 to 5 wt. %, more preferably from 0.005 to 1 wt. %. The total amount of Components (b) and (c) is preferably from 0.1 to 80 wt. %, more preferably from 1 to 40 wt. % (which will hereinafter be called "%", simply) from the viewpoint of fecal condition improving effect.

Sufficient improvement in bowel movement and intestinal regulation effect cannot be attained unless both of Components (b) and (c) are contained.

Viscosity of 5% aqueous solutions of each dietary fiber Component (b) and Component (c) is preferably 40 mPa·s or less, more preferably from 5 to 20 mPa·s at 20° C.

In consideration of bowel movement improving effect and intestinal regulation effect, Component (c) is added preferably in an amount of from 0.05 to 20 parts by weight (more preferably, from 0.1 to 10 parts by weight, more preferably from 0.3 to 3 parts by weight) relative to 1 part by weight of Component (b). Ratios of Component (c) to Component (b) within the above-described range are preferred because $CO_2$ gas due to a short-chain fatty acid generated by the reaction is not emitted so much and discomfort such as abdominal bloating or the like does not occur.

The fecal condition improving composition of the present invention may contain, in addition to the above-described components, another fecal condition improver (such as calcium polycarbophil and choline agonist), vitamins (vitamin A, vitamin $B_1$, $B_2$, $B_6$, $B_{12}$, vitamin C, vitamin D, and vitamin E); and another component having fecal condition improving action (enteric bacteria such as bifidobacteria, oligosaccharide, and sugar alcohol). The composition of the present invention mixed with a pharmaceutically acceptable carrier is administered as tablets, granules, subtle granules, pills, powders, capsules (both hard capsules and soft capsules), troches, chewables and liquids (tonic drinks).

The dosage of the fecal condition improving composition is preferably 5 g per adult administered once to three times a day. The fecal condition improving composition of the present invention is effective for constipation due to irritable bowel syndrome.

EXAMPLES

Example 1

Evaluation of Improvement in Fecal Condition

A beverage having the following composition was prepared.

| | |
|---|---|
| Chlorogenic acid | 0.2% |
| Molecular-weight-reduced sodium alginate | 2.4 |
| (viscosity of its 5% aqueous solution: 10 mPa · s, 20° C.) | |
| Molecular-weight-reduced hemicellulose | 3 |
| (viscosity of its 5% aqueous solution: about 7 mPa · s, 20° C.) | |
| Reduced maltose syrup | 5 |
| Flavor | 0.1 |
| Citric acid | 0.1 |
| Water | balance |
| Total | 100 |

Five males suffering from daily abdominal pain or diarrhea during commute took 125 mL of the beverage every morning before leaving home for 5 days and whether their abdominal pain or diarrhea was ameliorated or not was evaluated. Of the five males, three recognized substantial relief of the abdominal pain or occurrence of no diarrhea, one recognized slight relief and one recognized no improvement.

In a similar manner, a beverage obtained by omitting only chlorogenic acid from the above-described composition (Comparative Product 1), a beverage obtained by omitting only molecular-weight-reduced sodium alginate from the above-described composition (Comparative Product 2), and a beverage obtained by omitting only molecular-weight-reduced hemicellulose (Comparative Product 3) were each administered to five males suffering from abdominal pain or diarrhea in an amount of 125 mL for 5 days and evaluation was performed similarly. One male recognized substantial relief in each of Comparative Product 1, Comparative Product 2 and Comparative Product 3, one male recognized slight relief in each of Comparative Product 1, Comparative Product 2 and Comparative Product 3, and three males recognized no particular improvement in each product.

Evaluation was done similarly by using a beverage (Comparative Product 4) obtained by incorporating and dispersing cellulose, that is, a non-water-soluble dietary fiber instead of molecular-weight-reduced sodium alginate in the above-described composition. One recognized a substantial relief, one recognized a slight relief and three recognized no particular improvement.

Example 2

A beverage having the below-described composition was prepared. It has been confirmed that daily administration of 100 mL of the beverage brought about an evident fecal condition improving effect.

| | |
|---|---|
| Coffee bean extract ("Flavor Holder FH1041", product of T. Hasegawa Co., Ltd., chlorogenic acid content: 30%) | 1% |
| Molecular-weight-reduced Na alginate (same as that employed in Example 1) | 3 |
| Indigestible dextrin ("Fibersol 2", product of Matsugaya Chemical) | 5 |
| Reduced maltose syrup | 3 |
| Flavor | 0.2 |
| Citric acid | 0.3 |
| Water | Balance |
| Total | 100 |

Example 3

A beverage having the below-described composition was prepared. It has been confirmed that daily administration of 100 mL of the beverage brought about an evident fecal condition improving effect.

| | |
|---|---|
| Coffee bean extract ("Flavor Holder FH1041", product of T. Hasegawa Co., Ltd., chlorogenic acid content: 30%) | 0.4% |
| Molecular-weight-reduced Na alginate (same as that employed in Example 1) | 3 |
| Molecular-weight-reduced guar gum (viscosity of its 5% aqueous solution: 5 mPa·s, 20° C.) | 3 |
| Reduced maltose syrup | 3 |
| Flavor | 0.2 |
| Citric acid | 0.3 |
| Water | Balance |
| Total | 100 |

Example 4

Fecal Condition Improver (Chewable tablet)

To 48.5 parts by weight of chewable tablet powder composed of 15% of a mixed vitamin preparation containing vitamin $B_1$ nitrate, vitamin $B_2$, vitamin $B_6$ and vitamin C, 60% of frost sugar, 21.5% of dextrin, 3% of sucrose ester and 0.5% of flavor were added 1.5 parts by weight of a coffee bean extract ("Flavor Holder FH1041", product of T. Hasegawa Co., Ltd., chlorogenic acid content: 30%), 25 parts by weight of molecular-weight-reduced sodium alginate (same as that employed in Example 1) and 25 parts by weight of molecular-weight-reduced hemicellulose (same as that employed in Example 1). The resulting mixture was tableted in a conventional manner into tablets each weighing 0.5 g, whereby chewable tablets with excellent flavor to be used for the purpose of improving fecal condition were obtained.

It has been confirmed that daily administration of 10 chewable tablets thus obtained brought about the effect of the present invention for both constipation and diarrhea of irritable bowel syndrome.

INDUSTRIAL APPLICABILITY

The composition of the present invention is useful as a less-stimulating food or beverage, or a pharmaceutical for improving the fecal condition of humans or animals, more specifically, for ameliorating constipation by inhibiting intestinal clamping due to imbalance of the autonomic nervous system caused by psychological stress or dietary changes, suppressing abdominal pain or discomfort, improving the fecal condition, and ameliorating constipation.

The invention claimed is:

1. A fecal condition improving composition, which comprises the following components (a), (b) and (c):
    (a) 0.001 to 5 wt. % of at least one compound selected from the group consisting of caffeic acid, chlorogenic acid and ferulic acid, esters thereof, and pharmaceutically acceptable salts thereof,
    (b) a water-soluble and hardly-fermentable dietary fiber which is at least one selected from the group consisting of molecular-weight-reduced alginic acid and a salt thereof, and
    (c) a water-soluble and fermentable dietary fiber which is at least one selected from the group consisting of molecular-weight-reduced hemicellulose, indigestible dextrin and molecular weight reduced guar gum
    wherein Components (b) and (c) are present in a total amount of 0.1 to 80 wt. %
    and a viscosity of a 5% aqueous solution of each dietary fiber Component (b) and Component (c) is 40 mPa·s or less.

2. The fecal condition improving composition according to claim 1, wherein a weight ratio of Component (a) to the total amount of Components (b) and (c) is 1/1000 to 10/1.

3. The fecal condition improving composition according to claim 1, wherein Component (c) is present in an amount of 0.05 to 20 parts by weight relative to 1 part by weight of Component (b).

4. A fecal condition improving method, which comprises administering to a patient in need thereof, an effective amount of the composition of claim 1.

5. The method according to claim 4, wherein said composition is administered in an amount of 5 g, one to three times a day.

6. The method according to claim 4, wherein a weight ratio of Component (a) to the total amount of Components (b) and (c) is 1/1000 to 10/1.

7. The method according to claim 4, wherein Component (c) is present in an amount of 0.05 to 20 parts by weight relative to 1 part by weight of Component (b).

* * * * *